(12) United States Patent
Knight

(10) Patent No.: US 11,801,376 B2
(45) Date of Patent: Oct. 31, 2023

(54) MEDICAL FOUR-WAY STOPCOCKS WITH LOW RESIDUAL SIDE PORT VOLUME

(71) Applicant: Codan US Corporation, Santa Ana, CA (US)

(72) Inventor: Thomas F. Knight, Santa Ana, CA (US)

(73) Assignee: CODAN US CORPORATION, Santa Ana, CA (US)

( * ) Notice: Subject to any disclaimer, the term of this patent is extended or adjusted under 35 U.S.C. 154(b) by 117 days.

(21) Appl. No.: 16/938,833

(22) Filed: Jul. 24, 2020

(65) Prior Publication Data

US 2022/0023610 A1 Jan. 27, 2022

(51) Int. Cl.
*A61M 39/22* (2006.01)
*A61M 39/26* (2006.01)

(52) U.S. Cl.
CPC ..... *A61M 39/223* (2013.01); *A61M 2039/229* (2013.01); *A61M 2039/268* (2013.01); *Y10T 137/86863* (2015.04)

(58) Field of Classification Search
CPC ........... A61M 39/223; A61M 2039/229; Y10T 137/86863
See application file for complete search history.

(56) References Cited

U.S. PATENT DOCUMENTS

| | | | | |
|---|---|---|---|---|
| 3,481,367 A | * | 12/1969 | Deuschle | B23B 33/005 251/368 |
| 4,197,876 A | * | 4/1980 | Lobdell | F16K 5/045 251/366 |
| 4,219,021 A | * | 8/1980 | Fink | A61M 39/223 137/556.6 |
| 4,314,586 A | * | 2/1982 | Folkman | F16K 11/0853 251/368 |
| 5,807,312 A | * | 9/1998 | Dzwonkiewicz | A61M 5/1424 604/32 |
| 6,099,511 A | * | 8/2000 | Devos | A61M 5/1408 604/82 |
| 6,287,265 B1 | * | 9/2001 | Gleason | A61B 5/150992 600/573 |
| 6,497,250 B1 | * | 12/2002 | Johann | F16K 11/0853 137/625.46 |
| 6,729,350 B2 | * | 5/2004 | Schick | F16K 11/074 137/625.46 |
| 6,969,045 B2 | * | 11/2005 | Salven | F16K 27/045 251/304 |

(Continued)

*Primary Examiner* — Craig M Schneider
*Assistant Examiner* — Christopher D Ballman
(74) *Attorney, Agent, or Firm* — Kutak Rock LLP

(57) ABSTRACT

In general, one aspect disclosed features a medical device, comprising: a four-way medical stopcock, comprising: a body defining a cock barrel and comprising: a first stem having a first port, a second stem having a second port, and a side stem having a side port; and a rotatable cock disposed within the cock barrel, wherein: the cock places the first port and second port in fluid communication when the cock is in a first position, and the cock places the first port, second port, and side port in fluid communication when the cock is in a second position; and a needleless valve having a valve stem, wherein the valve stem is disposed within the side stem such that an internal volume defined by the side stem, the valve stem, and the cock when the cock is in the third position, is approximately 0.09 ml.

25 Claims, 7 Drawing Sheets

(56) References Cited

U.S. PATENT DOCUMENTS

| | | | | |
|---|---|---|---|---|
| 7,132,650 B1* | 11/2006 | Gamble | ........... | G01N 30/80 |
| | | | | 250/288 |
| 7,232,420 B1* | 6/2007 | Abulhaj | ........... | A61M 5/1411 |
| | | | | 604/32 |
| 7,506,664 B2* | 3/2009 | Norris | ........... | F16K 11/0876 |
| | | | | 137/625.42 |
| 7,963,951 B2* | 6/2011 | Kitani | ........... | A61M 39/223 |
| | | | | 137/625 |
| 8,833,394 B2* | 9/2014 | McCoy | ........... | F16K 5/0442 |
| | | | | 251/288 |
| 9,259,527 B2* | 2/2016 | Spohn | ........... | A61M 39/223 |
| 9,345,640 B2* | 5/2016 | Mosler | ........... | A61J 1/2075 |
| 9,375,561 B2* | 6/2016 | Mansour | ........... | A61M 39/223 |
| 9,585,812 B2* | 3/2017 | Browka | ........... | A61J 1/2086 |
| 9,775,981 B2* | 10/2017 | Nelson | ........... | A61M 39/223 |
| 2004/0210162 A1* | 10/2004 | Wyatt | ........... | A61B 5/150992 |
| | | | | 600/573 |
| 2007/0219483 A1* | 9/2007 | Kitani | ........... | A61M 39/26 |
| | | | | 604/32 |
| 2008/0067462 A1* | 3/2008 | Miller | ........... | A61M 39/22 |
| | | | | 251/149.1 |
| 2018/0036480 A1* | 2/2018 | Riphagen | ........... | A61L 31/14 |

* cited by examiner

Notes: All dimensions are .xxx ± .005

MEDICAL FOUR-WAY STOPCOCKS WITH LOW RESIDUAL SIDE PORT VOLUME

DESCRIPTION OF RELATED ART

The disclosed technology relates generally to medical devices, and more particularly some embodiments relate to medical stopcocks.

SUMMARY

In general, one aspect disclosed features a medical device, comprising: a four-way medical stopcock, comprising: a body defining a cock barrel and comprising: a first stem having a first port, a second stem having a second port, and a side stem having a side port; and a rotatable cock disposed within the cock barrel, wherein: the cock places the first port and second port in fluid communication when the cock is in a first position, and the cock places the first port, second port, and side port in fluid communication when the cock is in a second position; and a needleless valve having a valve stem, wherein the valve stem is disposed within the side stem such that an internal volume defined by the side stem, the valve stem, and the cock when the cock is in the third position, is approximately 0.09 ml.

Embodiments of the four-way medical stopcock may include one or more of the following features. In some embodiments, the valve stem is fixed within the side stem with an ultraviolet-curable adhesive. In some embodiments, a distance between the valve stem and the cock is approximately 0.005 in. In some embodiments, a medical device comprises a plurality of the four-way medical stopcocks; and a gang plate physically coupled to each of the plurality of the four-way medical stopcocks.

In general, one aspect disclosed features a medical device, comprising: a four-way medical stopcock, comprising: a body defining a cock barrel and comprising: a first stem having a first port, a second stem having a second port, and a side stem having a side port; and a rotatable cock disposed within the cock barrel, wherein: the cock places the first port and second port in fluid communication when the cock is in a first position, and the cock places the first port, second port, and side port in fluid communication when the cock is in a second position; and a male Luer lock having a Luer lock stem; wherein the Luer lock stem is disposed within the side stem such that an internal volume defined by the side stem, the Luer lock stem, and the cock when the cock is in the third position, is approximately 0.025 ml.

Embodiments of the medical device may include one or more of the following features. In some embodiments, a distance between the Luer lock stem and the cock is approximately 0.005 in. Some embodiments comprise a medical device comprising: a plurality of the four-way medical stopcocks; and a gang plate physically coupled to each of the plurality of the four-way medical stopcocks.

In general, one aspect disclosed features a medical device, comprising: a four-way medical stopcock, comprising: a body defining a cock barrel and comprising: a first stem having a first port, a second stem having a second port, and a side stem having a side port; and a rotatable cock disposed within the cock barrel, wherein: the cock places the first port and second port in fluid communication when the cock is in a first position, and the cock places the first port, second port, and side port in fluid communication when the cock is in a second position; and a fluid transport device having a device stem; wherein the device stem is disposed within the side stem such that a distance between the device stem and the cock is approximately 0.005 in.

Embodiments of the medical device may include one or more of the following features. In some embodiments, the device stem is fixed within the side port with an ultraviolet-curable adhesive. In some embodiments, the fluid transport device is a needleless valve. In some embodiments, the device stem is disposed within the side stem such that an internal volume defined by the side stem, the device stem, and the cock when the cock is in the third position, is approximately 0.09 ml. In some embodiments, the fluid transport device is a male Luer lock. In some embodiments, the device stem is disposed within the side stem such that an internal volume defined by the side stem, the device stem, and the cock when the cock is in the third position, is approximately 0.025 ml. Some embodiments comprise a medical device comprising: a plurality of the four-way medical stopcocks; and a gang plate physically coupled to each of the plurality of the four-way medical stopcocks.

In general, one aspect disclosed features a method for manufacturing a medical device, comprising: providing a four-way medical stopcock, comprising: a body defining a cock barrel and comprising: a first stem having a first port, a second stem having a second port, and a side stem having a side port; and a rotatable cock disposed within the cock barrel, wherein: the cock places the first port and second port in fluid communication when the cock is in a first position, and the cock places the first port, second port, and side port in fluid communication when the cock is in a second position; and providing a fluid transport device having a device stem; disposing the device stem within the side stem such that a distance between the device stem and the cock is approximately 0.005 in.

Embodiments of the method may include one or more of the following features. Some embodiments comprise fixing the device stem within the side port with an ultraviolet-curable adhesive. In some embodiments, providing a fluid transport device having a device stem comprises: providing a needleless valve. Some embodiments comprise disposing the device stem within the side stem such that an internal volume defined by the side stem, the device stem, and the cock when the cock is in the third position, is approximately 0.09 ml. In some embodiments, providing a fluid transport device having a device stem comprises: providing a male Luer lock. Some embodiments comprise disposing the device stem within the side stem such that an internal volume defined by the side stem, the device stem, and the cock when the cock is in the third position, is approximately 0.025 ml. Some embodiments comprise ganging together a plurality of the four-way medical stopcocks of claim.

BRIEF DESCRIPTION OF THE DRAWINGS

The present disclosure, in accordance with one or more various embodiments, is described in detail with reference to the following figures. The figures are provided for purposes of illustration only and merely depict typical or example embodiments.

The figures are not exhaustive and do not limit the present disclosure to the precise form disclosed.

DETAILED DESCRIPTION

Embodiments of the disclosure provide medical four-way stopcocks with low residual side port volume. Four-way medical stopcocks are valves that provide four-way fluid flow by turning a handle on the top of the stopcock. These stopcocks can be used, for example, to reduce two lines to one, to infuse drugs into a flow of saline solution, to add extension lines, and the like.

Figure 1:
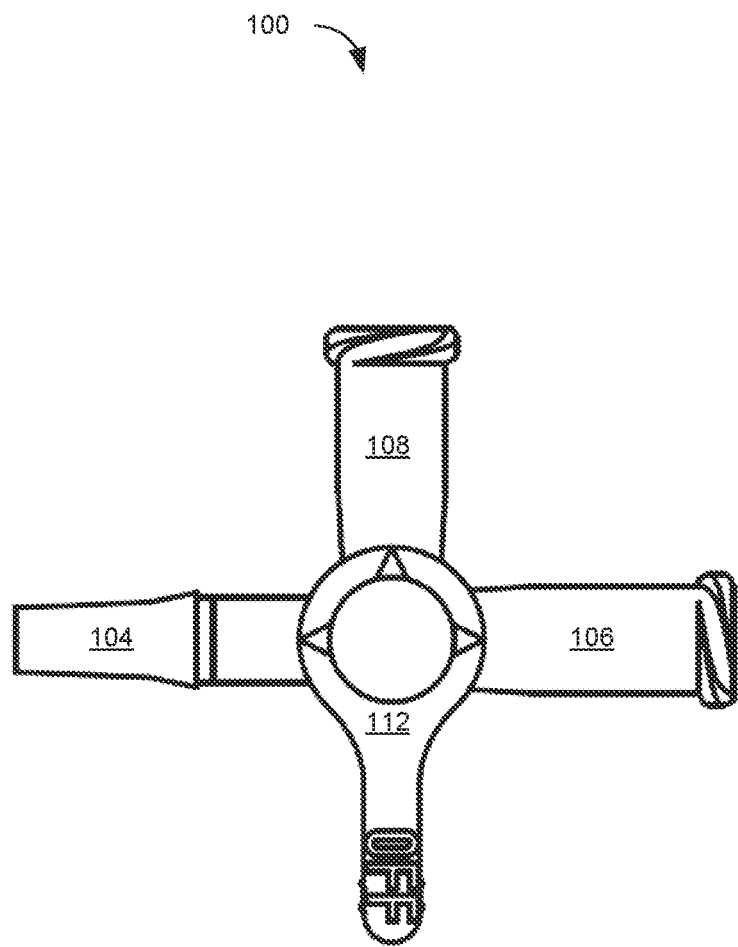
FIG. 1 shows a conventional four-way stopcock.

FIG. 1 shows a conventional four-way stopcock 100. The stopcock 100 includes a body that includes three stems 104, 106, and 108. The coaxial stems 104 and 106 are generally used to pass a flow of fluid, while the side stem 108 is generally used to introduce medicine into the flow. The body 102 of the stopcock defines a barrel within which a rotatable cock 112 is disposed. By rotating the cock 112, a user can allow a fluid flow through stems 104 and 106, interrupt that flow, add medicine from the side stem 108 to the flow, and the like.

One problem with these conventional four-way stopcocks is that, once fluid is introduced through the side stem 108 and then stopped by rotating the cock 112, a substantial amount of that fluid remains trapped in the side stem 108. Before resuming the flow of fluid through the side stem 108, or introducing another fluid through the side stem 108, the trapped residual fluid must be flushed, that is, removed and discarded. This flushing procedure requires separating one or more fluid lines from the stopcock, which not only takes time, but also increases the risks of breakage, infection, and the like.

Figure 2:
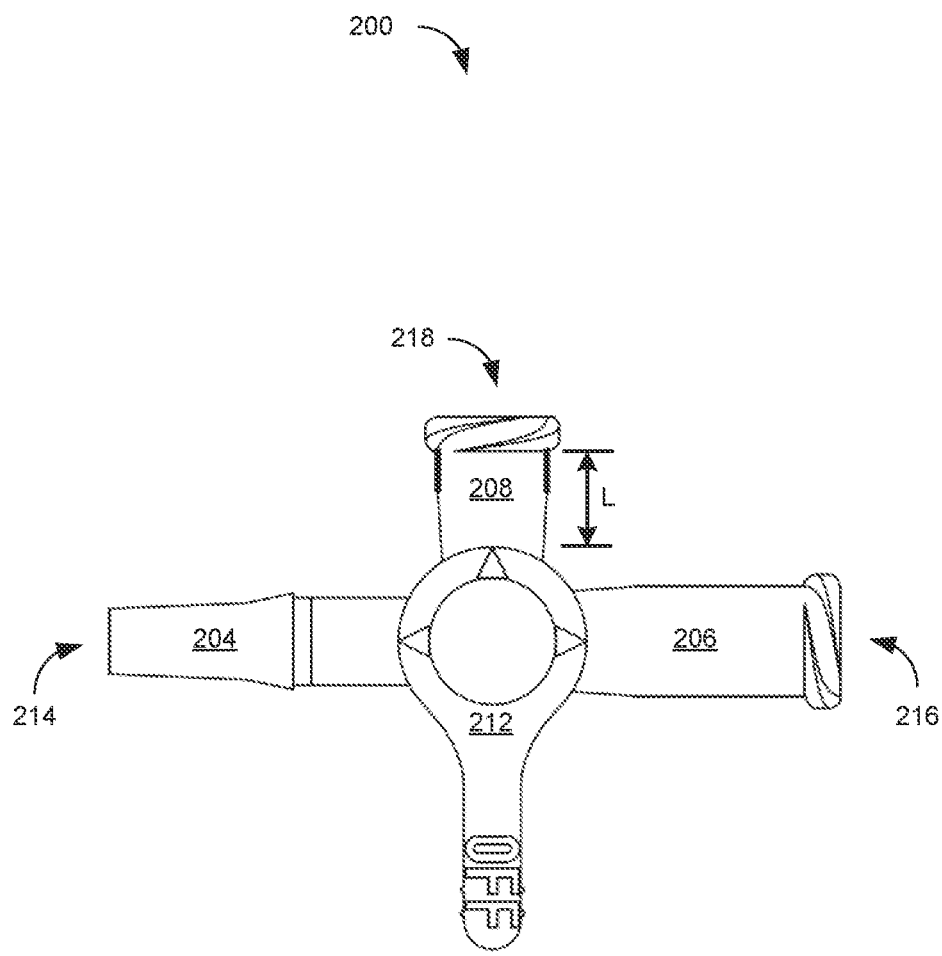
FIG. 2 shows a four-way stopcock according to embodiments of the disclosed technology.

The disclosed embodiments reduce the amount of this residual, to the point where flushing may not be needed in most cases. FIG. 2 shows a four-way stopcock 200 according to embodiments of the disclosed technology. Referring to FIG. 2, the four-way stopcock 200 may include three stems 204, 206, and 208, each having a respective port 214, 216, and 218. The coaxial stems 204 and 206 are generally used to pass a flow of fluid, while the side stem 208 is generally used to introduce medicine into the flow. However, the disclosed stopcocks may be used in other ways.

The body 202 of the stopcock defines a barrel within which a rotatable cock 212 is disposed. By rotating the cock 212, a user can allow a fluid flow through stems 204 and 206, interrupt that flow, add medicine from the side stem 208 to the flow, and the like. For example, all three ports 214, 216, and 218 may be placed in fluid communication when the cock 212 is in the position shown in FIG. 1. By rotating the cock 112 a half turn from the position shown in FIG. 1, only the coaxial ports 214 and 216 may be placed in fluid communication. By rotating the cock 112 clockwise a quarter turn from the position shown in FIG. 1, only the ports 216 and 218 may be placed in fluid communication. By rotating the cock 112 counterclockwise a quarter turn from the position shown in FIG. 1, only the ports 214 and 218 may be placed in fluid communication. Other positions of the cock 112 may prevent any fluid communication among the ports 214, 216, and 218.

In some embodiments, the length L of the side stem 208 is significantly less than the length of the side stem 108 of the conventional stopcock 100. In some embodiments, the length L of the side stem 208 may be half that of the side stem 108 of the conventional stopcock 100. For example, in some embodiments, L may be approximately one quarter inch, while in conventional stopcocks this length may be approximately one half inch.

Figure 3:
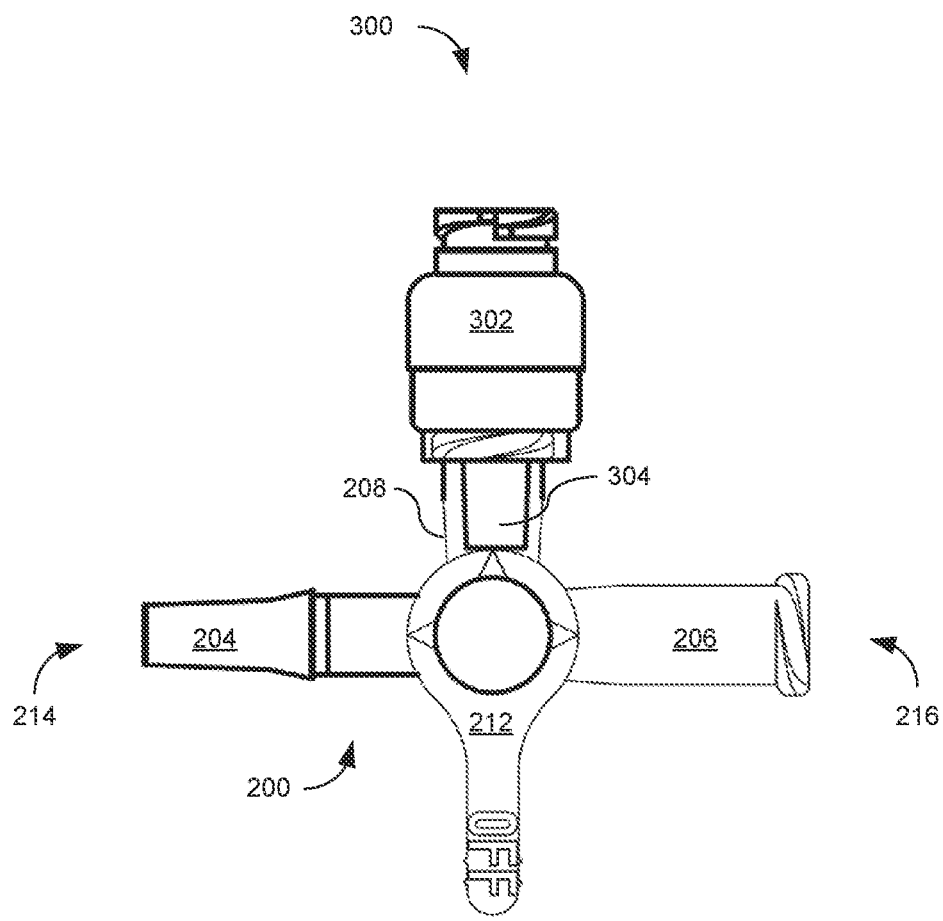
FIG. 3 shows a medical device including a four-way stopcock and a needleless valve with a valve stem according to embodiments of the disclosed technology.
Figure 4:
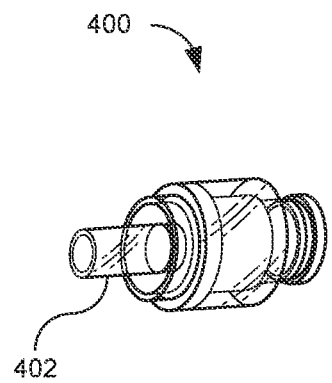
FIG. 4 is a perspective view of a needleless valve having an elongated valve stem according to embodiments of the disclosed technology.
Figure 5:
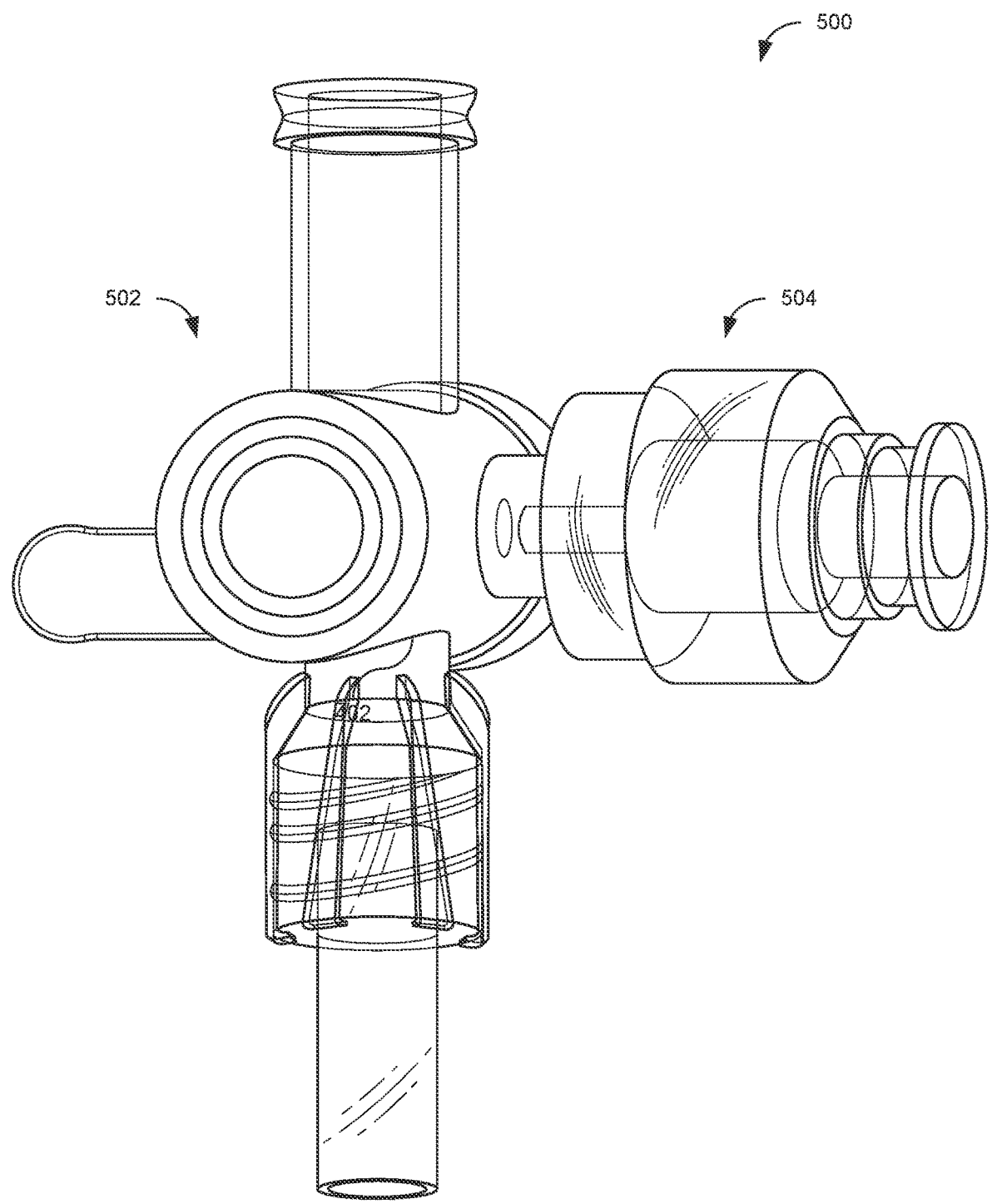
FIG. 5 is a perspective view of a medical device comprising a four-way stopcock and a needleless valve according to embodiments of the disclosed technology.

In some embodiments, a fluid transport device having a stem may be attached to the side stem 208. FIG. 3 shows a medical device 300 including a four-way stopcock and a needleless valve with a valve stem according to embodiments of the disclosed technology. Referring to FIG. 3, the four-way stopcock may be implemented in the same manner as the four-way stopcock 200 of FIG. 2. Conventional needleless valves generally have no stem, but instead are sonically welded to other medical devices. In contrast, the disclosed needleless valve 302 may include a valve stem 304 that is disposed within the side stem 208 of the four-way stopcock 200, as shown in FIG. 3. The dimensions of the valve stem 304 may be selected to reduce or minimize the amount of fluid that may be trapped in the side stem 208 when the cock 212 is closed. For example, the valve stem 304 may be longer than conventional valve stems. FIG. 4 is a perspective view of a needleless valve 400 having an elongated valve stem 402 according to embodiments of the disclosed technology. FIG. 5 is a perspective view of a medical device 500 comprising a four-way stopcock 502 and a needleless valve 504 according to embodiments of the disclosed technology.

Figure 6:
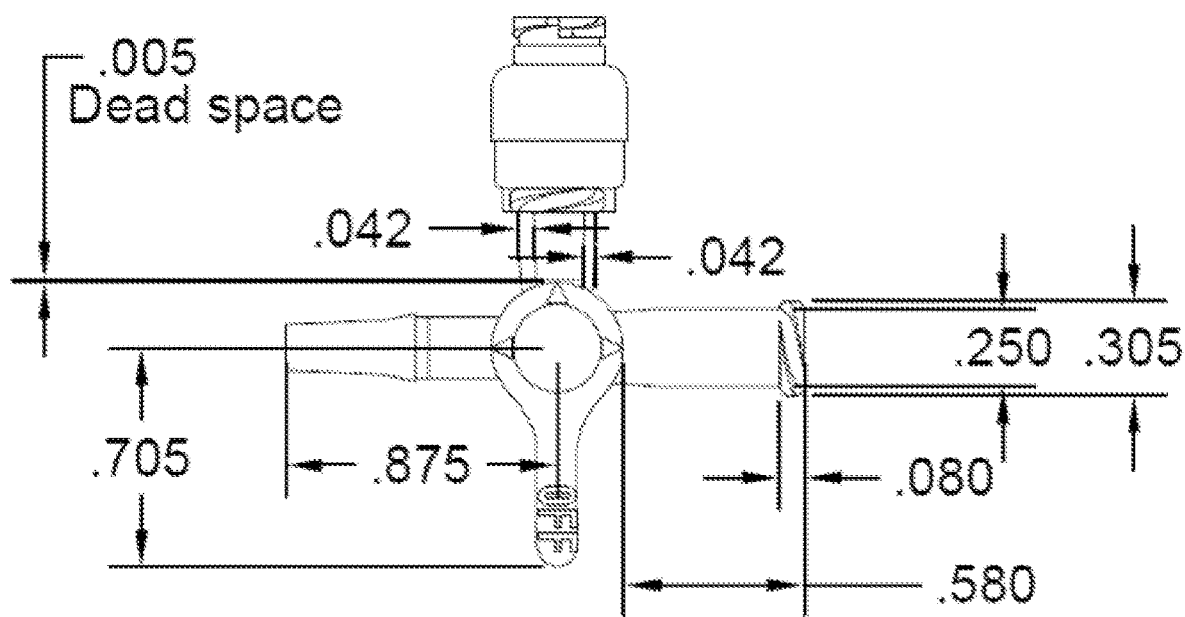
FIG. 6 shows dimensions of a four-way stopcock and a needleless valve according to embodiments of the disclosed technology.

In some embodiments, the valve stem 304 may be disposed within the side stem 208 such that an internal volume defined by the side stem, the valve stem, and the cock when the cock is in the third position (that is, closed to the side stem), is approximately 0.09 ml. In some embodiments, the valve stem 304 may be disposed within the side stem 208 such that a distance between the valve stem 304 and the cock 212 ("Deadspace") is approximately 0.005 in, as shown in FIG. 6.

Figure 7:
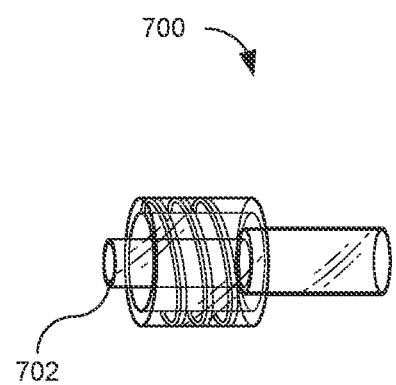
FIG. 7 is a perspective view of a male Luer lock having an elongated male Luer lock stem according to embodiments of the disclosed technology.

While in the described embodiments the fluid transport device is implemented as a needleless valve, other embodiments may implement the fluid transport device in other ways. For example, the fluid transport device may be implemented as a male Luer lock, a syringe, or the like. When the fluid transport device is implemented as a male Luer lock, an internal volume defined by the side stem, the male Luer lock stem, and the cock when the cock is in the third position (that is, closed to the side stem), is approximately 0.025 ml. FIG. 7 is a perspective view of a male Luer lock 700 having an elongated male Luer lock stem 702 according to embodiments of the disclosed technology.

The described embodiments may feature both a short side stem and a fluid transport device with a long stem. This combination significantly reduces the amount of fluid trapped in the side stem when the cock of the stopcock is closed. Other embodiments may feature only the short side stem, or only a fluid transport device with a long stem. These embodiments also reduce the amount of fluid trapped in the side stem when the cock of the stopcock is closed, but not to the degree of the described embodiments.

For example, the medical device 300 of FIG. 3 may be implemented with a conventional stopcock having a long side stem. In such a long side stem embodiment, with the fluid transport device implemented as a male Luer lock, the a male Luer lock stem may be disposed within the side port such that an internal volume defined by the side stem, the valve stem, and the cock when the cock is in the third position (that is, closed to the side stem), is approximately 0.076 ml. In such a long side stem embodiment, with the fluid transport device implemented as a needleless valve, the valve stem may be disposed within the side port such that an internal volume defined by the side stem, the valve stem, and the cock when the cock is in the third position (that is, closed to the side stem), is approximately 0.18 ml.

In some embodiments, the components of the stopcock and fluid transport device may be fabricated from polycarbonate, acrylic, or other suitable materials. For example, the body may be formed from macrylon polycarbonate. For example, the cock may be formed from polysulfone. In some embodiments, the fluid transport device may be fixed within the side stem with an ultraviolet-curable adhesive. For example, in embodiments where the fluid transport device is a needleless valve, the valve stem may be fixed within the side stem with an ultraviolet-curable adhesive. In these embodiments, a small space is left between the fluid transport device stem outer surface and the stopcock side stem inner surface to accommodate the adhesive. In embodiments not using adhesive, the fit between the fluid transport device stem and the stopcock side stem may be an interference fit.

In some embodiments, a medical device may be implemented by ganging together multiple stopcocks together and fluid transport devices. For example, multiple units of the medical device 300 of FIG. 3 may be mounted on a gang plate such that the coaxial stems 204 and 206 of adjacent stopcocks are interconnected in fluid communication.

Figure 8:
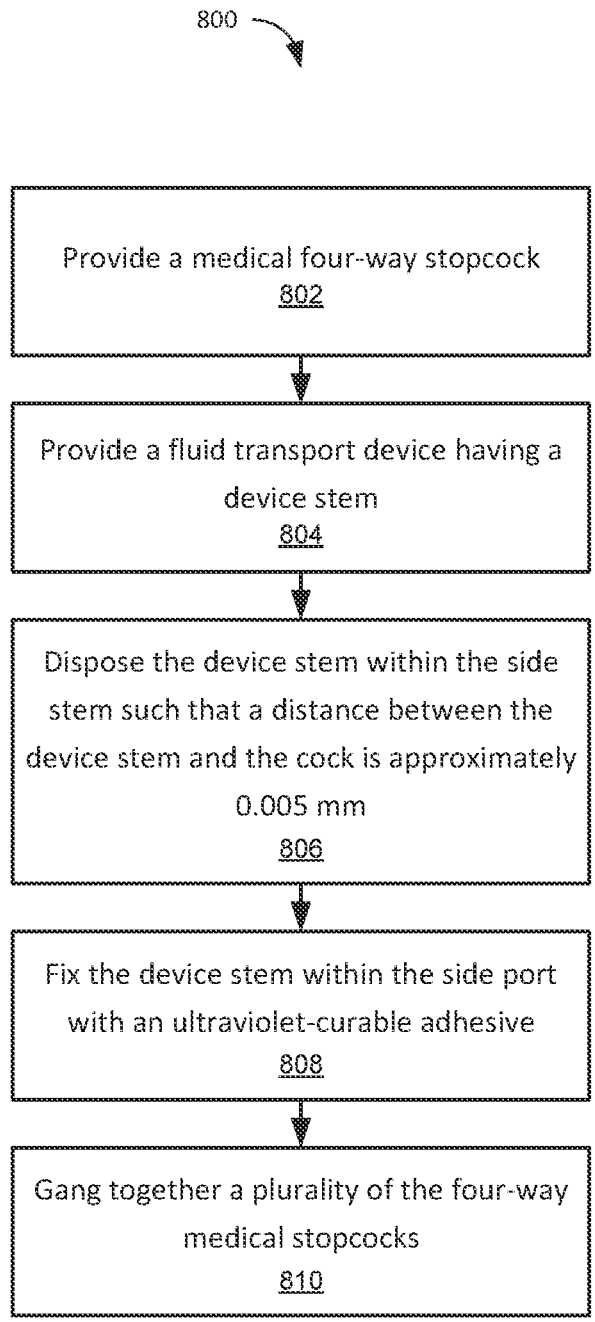
FIG. 8 is a flowchart for a process for manufacturing medical devices according to embodiments of the disclosed technology.

FIG. 8 is a flowchart for a process 800 for manufacturing medical devices according to embodiments of the disclosed technology. While elements of the process 800 are shown in one order, it should be understood that one or more elements may be performed in other orders, in parallel, and omitted.

Referring to FIG. 8, the process 800 may include providing a four-way medical stopcock, at 802. For example, the provided stopcock may be the medical four-way stopcock 200 of FIG. 2 with the short side stem.

Referring again to FIG. 8, the process 800 may include providing a fluid transport device having a device stem, at 804. The fluid transport device may have an elongated device stem. For example, the fluid transport device may be a needleless valve such as the needleless valve of FIG. 4, a male Luer lock such as the male Luer lock of FIG. 7, a syringe, and the like.

Referring again to FIG. 8, the process 800 may include disposing the device stem within the side stem such that a distance between the device stem and the cock is approximately 0.005 in, at 806. For example, a valve stem of a needleless valve may be disposed within the side stem of a stopcock as shown in FIG. 6. In embodiments where the fluid transport device is implemented as a needleless valve, the valve stem may be disposed within the side stem such that an internal volume defined by the side stem, the device stem, and the cock when the cock is in the third position (that is, closed to the side stem), is approximately 0.09 ml. In embodiments where the fluid transport device is implemented as a male Luer lock, the valve stem may be disposed within the side stem such that an internal volume defined by the side stem, the device stem, and the cock when the cock is in the third position (that is, closed to the side stem), is approximately 0.025 ml.

Referring again to FIG. 8, the process 800 may include fixing the device stem within the side stem of the stopcock with an ultraviolet-curable adhesive, at 808, for example as described above.

The process 800 may include ganging together a plurality of the four-way medical stopcocks, at 810. For example, the stems of the stopcocks may be interconnected, and the stopcocks joined to a gang plate.

Embodiments of the disclosed technology provide several advantages over conventional approaches. Embodiments featuring short side stems and/or fluid transport devices having stems eliminate deadspace that can trap residual medicine, requiring another flushing step to purge the trapped medicine before continued use. Embodiments featuring fluid transport devices having stems, for example such as the disclosed needleless valves having valve stems, permit simple fabrication using ultraviolet-curable adhesive. Embodiments featuring short side stems also provide low device profiles, enabling easier operation in tight spaces.

As used herein, the term "or" may be construed in either an inclusive or exclusive sense. Moreover, the description of resources, operations, or structures in the singular shall not be read to exclude the plural. Conditional language, such as, among others, "can," "could," "might," or "may," unless specifically stated otherwise, or otherwise understood within the context as used, is generally intended to convey that certain embodiments include, while other embodiments do not include, certain features, elements and/or steps.

Terms and phrases used in this document, and variations thereof, unless otherwise expressly stated, should be construed as open ended as opposed to limiting. Adjectives such as "conventional," "traditional," "normal," "standard," "known," and terms of similar meaning should not be construed as limiting the item described to a given time period or to an item available as of a given time, but instead should be read to encompass conventional, traditional, normal, or standard technologies that may be available or known now or at any time in the future. The presence of broadening words and phrases such as "one or more," "at least," "but not limited to" or other like phrases in some instances shall not be read to mean that the narrower case is intended or required in instances where such broadening phrases may be absent.

What is claimed is:

1. A medical device, comprising:
    a four-way medical stopcock, comprising:
        a body defining a cock barrel and comprising:
            a first stem having a first port,
            a second stem having a second port, and
            a side stem having a side port; and
        a rotatable cock disposed within the cock barrel, wherein:
            the cock places the first port and second port in fluid communication when the cock is in a first position,
            the cock places the first port, second port, and side port in fluid communication when the cock is in a second position, and
            a length of the side stem is ¼ inch; and
    a needleless valve having a valve stem, wherein the valve stem is disposed within the side stem.

2. The four-way medical stopcock, of claim 1, wherein the valve stem is fixed within the side stem with an ultraviolet-curable adhesive.

3. The four-way medical stopcock, of claim 1, wherein a distance between the valve stem and the cock is 0.005 in.

4. A medical device comprising:
a plurality of the four-way medical stopcocks of claim 1; and
a gang plate physically coupled to each of the plurality of the four-way medical stopcocks.

5. The medical device of claim 1, wherein:
the valve stem is disposed within the side stem such that an internal volume defined by the side stem, the valve stem, and the cock when the cock is in the third position, is 0.09 ml.

6. A medical device, comprising:
a four-way medical stopcock, comprising:
a body defining a cock barrel and comprising:
a first stem having a first port,
a second stem having a second port, and
a side stem having a side port, wherein a length of the side stem is ¼ inch; and
a rotatable cock disposed within the cock barrel, wherein:
the cock places the first port and second port in fluid communication when the cock is in a first position, and
the cock places the first port, second port, and side port in fluid communication when the cock is in a second position; and
a male Luer lock having a Luer lock stem
wherein the Luer lock stem is disposed within the side stem.

7. The four-way medical stopcock, of claim 6, wherein a distance between the Luer lock stem and the cock is 0.005 in.

8. A medical device comprising:
a plurality of the four-way medical stopcocks of claim 6; and
a gang plate physically coupled to each of the plurality of the four-way medical stopcocks.

9. The medical device of claim 6, wherein:
the Luer lock stem is disposed within the side stem such that an internal volume defined by the side stem, the Luer lock stem, and the cock when the cock is in the third position, is 0.025 ml.

10. A medical device, comprising:
a four-way medical stopcock, comprising:
a body defining a cock barrel and comprising:
a first stem having a first port,
a second stem having a second port, wherein a length of the side stem is ¼ inch, and
a side stem having a side port; and
a rotatable cock disposed within the cock barrel, wherein:
the cock places the first port and second port in fluid communication when the cock is in a first position, and
the cock places the first port, second port, and side port in fluid communication when the cock is in a second position; and
a fluid transport device having a device stem;
wherein the device stem is disposed within the side stem.

11. The four-way medical stopcock, of claim 10, wherein the device stem is fixed within the side port with an ultraviolet-curable adhesive.

12. The four-way medical stopcock, of claim 10, wherein the fluid transport device is a needleless valve.

13. The four-way medical stopcock, of claim 12, wherein the device stem is disposed within the side stem such that an internal volume defined by the side stem, the device stem, and the cock when the cock is in the third position, is 0.09 ml.

14. The four-way medical stopcock of claim 10, wherein the fluid transport device is a male Luer lock.

15. The four-way medical stopcock of claim 14, wherein the device stem is disposed within the side stem such that an internal volume defined by the side stem, the device stem, and the cock when the cock is in the third position, is 0.025 ml.

16. A medical device comprising:
a plurality of the four-way medical stopcocks of claim 10; and
a gang plate physically coupled to each of the plurality of the four-way medical stopcocks.

17. The medical device of claim 10, wherein:
wherein the device stem is disposed within the side stem such that a distance between the device stem and the cock is 0.005 in.

18. A method for manufacturing a medical device, comprising:
providing a four-way medical stopcock, comprising:
a body defining a cock barrel and comprising:
a first stem having a first port,
a second stem having a second port, and
a side stem having a side port, wherein a length of the side stem is ¼ inch; and
a rotatable cock disposed within the cock barrel, wherein:
the cock places the first port and second port in fluid communication when the cock is in a first position, and
the cock places the first port, second port, and side port in fluid communication when the cock is in a second position; and
providing a fluid transport device having a device stem; and
disposing the device stem within the side stem.

19. The method of claim 18, further comprising:
fixing the device stem within the side port with an ultraviolet-curable adhesive.

20. The method of claim 18, wherein providing a fluid transport device having a device stem comprises:
providing a needleless valve.

21. The method of claim 20, further comprising:
disposing the device stem within the side stem such that an internal volume defined by the side stem, the device stem, and the cock when the cock is in the third position, is 0.09 ml.

22. The method of claim 18, wherein providing a fluid transport device having a device stem comprises:
providing a male Luer lock.

23. The method of claim 22, further comprising:
disposing the device stem within the side stem such that an internal volume defined by the side stem, the device stem, and the cock when the cock is in the third position, is 0.025 ml.

24. The method of claim 18, further comprising:
ganging together a plurality of the four-way medical stopcocks of claim 18.

25. The method of claim 18, further comprising:
disposing the device stem within the side stem such that a distance between the device stem and the cock is 0.005 in.

* * * * *